United States Patent [19]

Cope

[11] 4,174,389
[45] Nov. 13, 1979

[54] OPHTHALMIC USE OF COLLAGENASE

[76] Inventor: Louise A. Cope, 3803 University Blvd., Houston, Tex. 77005

[21] Appl. No.: 796,807

[22] Filed: May 13, 1977

[51] Int. Cl.$^2$ ............................................. A61K 37/48
[52] U.S. Cl. ...................................................... 424/94
[58] Field of Search .......................................... 424/94

[56] References Cited
PUBLICATIONS

Zolotov—Chem. Abst., vol. 82 (1975) 149384d.
O'Neill et al.—Chem. Abst., vol. 79 (1973) 49287u.
Smirnov—Chem. Abst., vol. 76 (1972), 30596k.

Primary Examiner—Sam Rosen
Attorney, Agent, or Firm—Charles H. De La Garza

[57] ABSTRACT

A method for the selective lysis of collagen fibrils located in the ocular region of a mammal comprising injecting into said ocular region an effective amount of a pharmacologically suitable solution comprising collagenase; and contacting said fibrils with said solution for a period of time sufficient to lyse said fibrils.

6 Claims, No Drawings

OPHTHALMIC USE OF COLLAGENASE

BACKGROUND OF THE INVENTION

Approximately one-third of the total protein in mammalian organisms is comprised of collagen; the main constituent of skin, tendon, cartilage, teeth and bone material is collagen. Mandl, I., COLLAGENASE, "Collagenase Comes of Age", p. 1 (Gordon and Breach, Science Publishers, Inc., 1972). Enzymes which degrade collagen are of importance in controlling conditions involving collagen rich tissue. Collagenase is effective in controlling such conditions.

The use of enzymes in the medical field is well known. For example, Collagenase produced from the bacterium *Clostridium histolyticum* has been used as a debridement agent. Other enzymes are used surgically in ophthalmology. For example, alphachymotrysin is used to lyse zonules in cataract surgery and hyaluronidase is used extraocularly as a means of spreading local anesthesia more effectively through tissue.

The use of enzymes and, in particular, collagenase has been disclosed in the art. Processes for the production of Collagenase from *Clostridium histolyticum* have been disclosed in U.S. Pat. Nos. 3,705,083 and 3,821,364. Processes for preparing other Collagenases have been disclosed in U.S. Pat. Nos. 3,267,006 and 3,677,900. Collagenase has been used in the treatment of herniated intervertebral discs of mammals and such treatment is disclosed in U.S. Pat. No. 3,678,158. Detoxified enzymes obtained from snake venom have been used in the treatment of ocular disorders as disclosed in U.S. Pat. No. 3,869,548.

The medical use of enzymes in the ocular region and, in particular, the medical use of collagenase in the ocular region presents the investigator with a multitude of problems. In general, the mammalian eyeball and surrounding tissue is comprised of a large quantity of collagen. Because of this, any injection or use of collagenase in the ocular region could potentially damage tissue not intended to be attacked by the collagenase.

The following brief discussion concerning basic ocular anatomy and opthalmic surgery serves to describe the many collagen rich structures of the ocular region and the problems facing opthalmic surgeons which are caused by the collagen rich structures.

Quite basically, the mammalian eyeball may be divided into an anterior and posterior portion, each of which has three layers. The outer most layer, the sclera, consists of tough connective tissue. The sclera is continuous with the transparent cornea anteriorly. The middle or vascular layer, properly called the choroid, is continuous anteriorly with the ciliary body and the pigmented portion of the eye, the iris. The retina comprises the internal layer of the eye.

The vitreous body is a transparent gel-like material which occupies approximately 80 percent of the posterior of the eyeball. On the anterior surface of the vitreous and posterior to the iris and pupil is the lens which is a transparent, biconvex and circular structure. The lens consists of many concentric layers of proteinaceous material surrounded by a capsule and held in position by suspensory ligaments.

Between the transparent cornea anteriorly and the iris posteriorly is the anterior chamber which contains aqueous humor. The anterior chamber is directly connected with the small posterior chamber of the eye via the pupillary opening. Aqueous humor is secreted by cells of the ciliary body. This fluid flows into the posterior chamber and through the pupil into the anterior chamber in order to nourish the cornea and maintain internal ocular pressure. In humans, this aqueous fluid is formed at an approximate rate of 2.1 microliters/minute. The volume of the anterior chamber is 0.25 milliliters and this fluid which flows into the chamber is filtered out through a system of channels in the trabecular meshwork.

The sclera, composed essentially of collagen, is a white, opaque covering of the eyeball and is continuous with the cornea. Anteriorly, the sclera is covered by the conjunctiva, a mucus membrane coating.

The cornea is composed of five layers, the corneal epithelium anteriorly, Bowman's membrane, the corneal stroma, Descement's membrane and the endothelium. The corneal epithelium is a continuation of the cells of the conjunctiva. The entire posterior cornea is covered by endothelial cells which function to maintain the cornea's crystalline clarity. Small molecules with a molecular weight of less than 6,200 can penetrate the endothelium membranes and enter the cornea. Molecules of larger molecular weight are unable to penetrate the endothelium. Bowman's membrane, the stroma, the Descement's membrane are all composed of collagen.

The lens is completely surrounded by a collagenous capsule. Beneath the anterior capsule are epithelial cells. The fibers of the lens are composed of hard crystalloid protein which is slowly secreted by the lens cells throughout life.

The iris, located at the anterior portion of the eye, is a thin circular disc which functions in a manner similar to the diaphragm of a camera. The iris consists of four layers: the anterior border layer, the stroma, the dilator muscle, and the posterior epithelium. Blood vessels located in the iris and the stroma contain collagenous tissue.

The trabecular meshwork is a system of filters located in the angle of the anterior chamber. This meshwork consists of a collection of collagenous pillars which are lined by endothelial cells. It is the trabecular meshwork through which the aqueous fluid flows by entering a gradually enlarging system of collector channels to enter the aqueous veins and ultimately leave the anterior portion of the eye.

The vitreous or hyaloid body is a transparent gel which is bound anteriorly by the lens and posteriorly by the internal limiting membrane of the retina. The attachment is strongest at the peripheral retina and the ciliary body. This attachment is known as the vitreous base. Basically, the vitreous consists of a three dimensional structure of straight collagen fibrils in whose interstices are loosely wound molecules of hyaluronic acid. The collagen fibrils are thickest at the peripheral vitreous, especially so at the vitreous base.

The retina consists of several cell layers. The outermost is the rod and cone layer which transforms light impulses into neurotransmitter impulses. Behind this layer lie the association neuronal cells. The innermost layers consist of ganglion cells which transmit information via the optic nerve to the brain. The inner limiting membrane is adjacent and posterior to the vitreous. Retinal blood vessels in the human run in the inner retinal layers and do not protrude into the vitreous. These retinal blood vessels contain collagen. In some animals, for example rabbits, these blood vessels protrude into the vitreous.

To summarize the human's ocular anatomy, a major portion of the protein constituent of the ocular region consists of collagen. In particular, the major protein constituent of the vitreous is collagen. Other ocular structures such as the cornea, and the trabecular meshwork contain collagen and each of these structures is lined by noncollagenous cells. Additionally, retinal blood vessels are comprised of collagenous material; however, these vessels lie within and not on the surface of the human retina.

The fact that many of the structures in the ocular region are composed of collagenous material would not appear to be of any great concern; however, many types of ophthalmic surgery, ocular region injuries, and ocular diseases, are complicated by structure rich in collagen fibrils. Moreover, intraocular scar formation which is a natural physiological response to trauma, including surgical trauma, can seriously affect vision since the intraocular space is so small and the many structures of the eye which are necessary for maintaining visual function are in close proximity. In many cases, glaucoma and retinal detachment are caused by intraocular scar formation. Additionally, scars formed on or under the conjunctiva, subconjunctival area, could damage the cornea and scars on the eyelids could impair proper visual function. Collagen is a major structural constituent of scars.

With regard to ophthalmic surgery, collagen rich structures of the human eye continue to complicate surgical procedures despite recent improvements and advancements in the surgical field. In particular, a collagen rich structure, properly named the vitreous, continues to complicate many ophthalmic surgical procedures including, but not limited to, cataract surgery, retinal detachment and pars plana vitrectomy.

In cataract surgery, the collagen rich fibrils of the vitreous may protrude into the anterior chamber and cause irreversible corneal edema or retinal detachment. Following cataract surgery, the iridovitreal adhesions may block the posterior-anterior passage of aqueous humor. The blocked aqueous accumulates posteriorly and pushes the collagen fibrils of the vitreous into the anterior chamber. If these fibrils touch and remain in contact with the cornea, edema, corneal deterioration, striate keratopathy and bullous keratopathy could result. *Current Concepts in Cataract Surgery,* (ed). Jared Emery and David Paton, C. V. Mosby (publ.), 1974, pg. 329-335.

Other complications of cataract surgery, corneal edema or retinal detachment, occur when the collagen fibrils of the vitreous draw up and become incorporated into the wound.

There are many causes of retinal detachment. Basically, traction is exerted on the retina through the vitreous base attachment and this traction may cause the damage to the retina by tearing it or by detaching it from the global wall.

For example, in many persons between the ages of 50 and 80 years, syneresis, or vitreous liquification, predisposes a hole to develop in the retina at an area of vitreous traction. Another widespread problem is diabetic retinopathy which is observed in about 50 percent of the individuals who have had diabetes for 10 years, 75 percent of those who have had it for 15 years, and 95 percent of those who have had it for 25 years. Although not all suffer from visual impairment, the disease is the leading cause of blindness in the United States among persons between the ages of 20 and 65. Approximately 48,000 individuals in this country are legally blind as a result of it. Maugh, F. A., Science, 192:539 (1976).

Retinopathy results from the diabetes-induced deterioration of the retinal microvasculature. The cause of this deterioration is unknown. In the eye, small vessels become leaky and occluded and, occasionally, new vessels form on the surface of the retina. In the more severe form of the disease, known as proliferative retinopathy, new blood vessels protrude into the vitreous and eventually rupture and hemorrhage into the vitreous. Finally, fibrous scar tissue forms in association with the new vessels. This tissue may exert traction on the retina and detach it.

For many years, ophthamologists experienced many complications which resulted from surgical manipulation of the vitreous such as chronic inflammation, macular edema, corneal edema, retinal detachment, glaucoma and septic endophthalmitis.

The number of difficulties were significantly reduced in 1968 when Kasner and associates demonstrated that an eye can function after removal of the vitreous, as it can after lens removal. Kasner, D., Miller, G. R. and Taylor, W. H., Trans. Am. Acad. Ophthalmol. Otolarynogol., 72:410-418 (1968). The technique for vitreous removal was the traumatic open-sky technique, wherein the vitreous was removed through a large limbal incision.

The surgical trauma was significantly reduced with Machemer and associates' discovery in 1971. Machemer, R., Bueffner, H., and Norton, E. W., Trans. Am. Acad. Ophthalmol. Otolarngo., 75:813-820 (1971). They, Machemer, et al., discovered an instrument called the vitreous infusion suction cutter (VISC) which can be used for removal of the vitreous. Improvements to this instrument have been developed since that time; however, retinal tears are still reported as a frequent complication of pars plana vitrectomy. Retinal tears or retinal detachment usually occur because of traction of the retina at the vitreous base.

R. G. Michaels in Volume 80 at pages 24-29 of the American Journal of Ophthalmology (1975) reported, in 100 consecutive cases of citrectomy, a 19 percent incidence of anterior tears near the sclerotomy site, a 16 percent incidence of anterior tears at other sites of firm vitreoretinal adhesion, and a three percent incidence of dialysis (large retinal tear) in other quadrants.

Because a major portion of the ocular region contains collagenous material, the injecting and contacting of any portion of the ocular region with collagenase can be potentially hazardous to the continued enjoyment of vision by the mammal and, in particular, the human. However, this is not to suggest that injections into the ocular region have not been made. Indeed, U.S. Pat. No. 3,869,548 discloses a method of and a medicament for the treatment of ocular disorders such as diabetic retinopathy and degenerative maculation of the eye. The medicament used was a detoxified enzyme obtained from the venom of snakes.

Further, in an article entitled "The Effects of Bacterial Collagenase in Rabbit Vitreous" published in Volume 8 of the Canadian Journal of Ophthalmology, researchers O'Neill and Shea disclose the injection of collagenase into the rabbit vitreous for the purpose of studying the nature of vitreous fibrosis and its treatment. The investigators reported that the collagenase broke down the normal fibrillar structure of the vitreous but also broke down the internal limiting membrane and affected the inner layers of the retina.

In an apparent attempt to limit the deleterious effects of collagenase, the investigators suggested that larger doses of the enzyme could be used for shorter periods of time, between 24 and 72 hours, and that an intravitreal solution containing a collagenase inhibitor could be administered. Alternatively, the investigators suggested that the adverse effects of the collagenase could be managed by washing the enzyme out with a balanced salt solution in a manner similar to that used when chymotrypsin is utilized in chemical zonulysis. These suggestions are not viable solutions to the problem of collagenase destroying tissue which is not intended to be destoyed.

SUMMARY OF THE INVENTION

The instant invention provides a solution to many of the difficulties facing ophthalmologists engaged in surgical practice and reduces the likelihood of detrimental effects of surgery by providing a method for the selective lysis of collagen fibrils located in the ocular region of a mammal comprising injecting into said ocular region an effective amount of a pharmacologically suitable solution comprising collagenase and contacting said fibrils with said solution for a short period of time. It should be understood by those skilled in the art that the period of time during which the collagenase containing solution is in contact with the collagen fibrils to be lysed is sufficient to lyse said fibrils without significant damage to other ocular structures not intended to be affected by the collagenase.

As used herein the words "ocular region" are intended to include the eye globe, subconjunctiva area and the eyelids. Further, "periocular" is intended to include the subconjunctiva and the eyelids. Still further, "injecting" or "injection" is intended to mean the administration by use of a syringe or any other suitable device as is well-known in the art.

In one feature of the present invention, the selective lysis of collagen fibrils located in the ocular region of a mammal is undertaken by injecting intravitreally an effective amount of a pharmacologically suitable solution comprising a concentrated amount of collagenase; contacting the selected collagen fibrils with said solution for a period of time sufficient to lyse the fibrils; and flushing the intravitreal region with a solution characterized by its inactivation of collagenase.

In one feature of the invention, flushing of the intravitreal region is comprised of the steps of: injecting an amount of a inactivator of collagenase solution; and removing the collagenase from the ocular region.

In another feature of the instant invention, the injecting and removing steps of the flushing step are performed substantially simultaneously.

In yet another feature of the instant invention, the lysis of selective collagen fibrils is performed by injecting an effective amount of a pharmacologically suitable solution comprising a concentrated amount of collagenase into the anterior chamber of the eye.

In yet other features of the instant invention, the lysis of collagen fibrils may be performed in the periocular tissue and, in particular, in the subconjunctival tissue for the purpose of lysing scar tissue.

In still another feature of the instant invention, the pharmacologically suitable solution is prepared by dissolving an effective amount of collagenase in a saline solution. The saline solution may be a balanced saline solution and should contain a sufficient quantity of calcium ions to activate the collagenase. If not 7.40, the pH of the saline solution should be adjusted to a physiologically compatible pH of 7.40 for maximum activation of the collagenase.

Another feature of the invention is the method for the selective lysis of collagen fibrils located in the ocular region of a mammal comprising: preparing a pharmacologically suitable solution comprising collagenase produced from the bacterium *Clostridium histolyticum* by admixing a concentrated amount of collagenase with a solution having a pH of about 7.40 and containing a sufficient amount of calcium ions to activate said collagenase; and injecting and contacting said collagen fibrils to be lysed with an effective amount of said pharmacologically suitable solution.

In another feature the said injection referred to in the above paragraph is made intravitreally and the above described method comprises the additional steps of: flushing collagenase from the intravitreal region by injecting into said intravitreal region an effective amount of a inactivator of collagenase solution and removing the collagenase from said intravitreal region.

In yet other features the injection may be made into the anterior chamber or the periocular tissue, including the subconjunctiva and the eyelids. When injections are made into these areas or regions mechanical flushing of the region is not required for the removal of collagenase.

DETAILED DESCRIPTION OF PREFERRED EMBODIMENTS

The ocular region of the mammal, and in particular the human, contains many collagen rich structures which are required for normal visual function. Selective lysis of collagen fibrils without further impairment of vision by the use of a collagenase containing solution would not appear to be appropriate and, indeed, would appear to be contrary to good ophthalmic practice. However, the instant invention overcomes many problems attendant to the injection of a solution of collagenase into the ocular region.

It should be understood that although it is preferred to utilize collagenase produced from the bacterium *Clostridium histolyticum,* other collagenases may be used in accordance with this invention. The particular type of collegenase used can be determined from a reasonable amount of routine experimentation and the following factors should be considered in selecting the type of collagenase to be used: the mammal injected; the nature and amount of the products formed from the lysis of collagen fibrils with the particular type of collagenase; the amount, location and nature of the collagen fibrils to be lysed; and the nature and proximity of other collagen rich structures adjacent the collagen fibrils to be lysed.

It has been discovered that the selective lysis of collagen fibrils located in the ocular region can be performed without undesirable side effects by injecting into the ocular region an effective amount of a pharmacologically suitable solution comprised of collagenase and contacting the selective collagen fibrils with said solution for a short period of time. In particular, this discovery can reduce the complications attendant to ophthalmic surgery such as cataract surgery, retinal detachment repair, and pars plana vitrectomy. Further, it can be used to reduce problems associated with scar tissue in the ocular region.

As previously stated, one complication of cataract extraction is the protrusion of the vitreous into the anterior chamber and the contact of the vitreous with the cornea. In such a situation, the immediate removal of the vitreous from the anterior chamber is indicated. If unremoved, irreversible corneal edema could occur.

In that situation and in accordance with the preferred embodiment of the instant invention, a minor but effective amount of a pharmacologically suitable solution comprising a concentrated amount of collagenase may be injected into the anterior chamber in order to lyse the collagen fibrils of the vitreous. The solution is allowed to contact the fibrils for a period of time sufficient to liquefy the fibrils. Once lysed the collagen fibrils are of no danger to the cornea; however, if desired, the lysed fibrils may be removed by the use of the vitreous infusion section cutter (VISC).

In this embodiment where the pharmacologically suitable solution is injected into the anterior chamber, there is no need to remove the solution from the chamber after it has contacted the collagen fibrils for a sufficient period of time since the natural flow of fluid through the chamber removes the solution from the eye before damage can occur to the lens or other structures containing exposed collagen. When injection is made into the anterior chamber the collagen fibrils of the protruding vitreous are selectively lysed because they are thinner and less dense than the collagen fibrils of the lens and other exposed collagen structures.

For a different reason, the exposed cornea and trabecular network are not destroyed by the collagenase solution since these structures are lined with endothelial cells. It has been found that these cells will not allow compounds with a molecular weight greater than 6200 to pass through the cell walls. Accordingly, collagenase which has a molecular weight many times greater than 6200 can not pass through the cell walls and destroy the collagen rich structures.

Another exposed structure, the collagen rich iris is protected anteriorly by the anterior border layer. In the blue iris the anterior border layer is thin and contains a few pigment cells; in the brown iris this layer is thick and contains many pigment cells.

When the method of the instant invention is performed in the periocular region and, in particular, the subconjunctival area or in the eyelids the remaining collagenase is not removed and may lyse some small blood vessels and cause minor hemorrhaging; however, the hemorrhages should disappear within a short period of time.

In the practice of the instant invention it is desirable that the eye be immobile during the procedure. Accordingly, either a local anesthetic such as Xylocaine or a tranquilizer such as Valium or Demerol may be administered. The amount and type of tranquilizer or anesthetic administered and the manner of administration may be determined in accordance with procedures well-known in the art.

In another embodiment of the instant invention, a minor but effective amount of a pharmacologically suitable solution comprising collagenase may be injected into the vitreous through the pars plana prior to vitrectomy. The solution may be left in contact with the collagen fibrils of the vitreous for a sufficient period of time in which to liquefy the vitreous; however, the solution should be flushed from the eye with a inactivator of collagenase. If left in the eye for a long period of time, damage could occur to other collagen-containing structures. Also, it is preferred that an inhibitor of collagenase not be injected to flush out the eye, since one problem with standard collagenase inhibitors, metal chelators, is that they also chelate metal ions essential for retinal metabolism. Accordingly, it is preferred to flush the eye with a solution which does not contain any collagenase activators.

It is preferred that the flush solution not have a physiologically compatible pH of 7.40 and not contain any free calcium ions. The pH of the flush solution may be either higher or lower than 7.40 but should not be so basic or acidic as to damage the internal structures of the eye. This type of solution will not activate the collagenase remaining in the ocular region. Further, it is preferred to inject the flush solution and simultaneously remove the resultant mixture from the intraocular region. This procedure may be undertaken by use of a double barrel irrigator/aspirator as is well-known and used in the art. If the collagenase were not removed from the inner ocular region, it could cause irreversible cataracts or other severe damage to the collagen rich structures of the inner eye.

It has been found that the pharmacologically suitable solution utilized in the practice of the instant invention may be produced by admixing a concentrated amount of collagenase with a buffer solution. The resultant mixture should not contain any compounds which could destroy or damage tissue in the ocular region other than that tissue sought to be selectively lysed.

In the preferred embodiment of this invention collagenase produced by the bacterium *Clostridium histolyticum* (Clostridiopeptidase A) is used; however, collagenase produced from other bacteria may be utilized in the practice of this invention. This preferred type of collagenase is commercially available from Advance Biofactures Corporation and is sold as Collagenase (Form III). It is a lyophillized powder that is shipped in a frozen state. It is preferred to maintain the lyophillized powder in a suitable dessicator at approximately $-20°$ C.

For maximum activity of the enzyme, the manufacturers recommend that the buffer solution used contain a concentration of approximately 0.33 molar of calcium ions and that the buffer solution be adjusted to a physiologically compatible pH of 7.40. This pH adjustment may be made by adding a sufficient amount of dilute solution of hydrochloric acid. The mixture or resultant solution should be kept on ice during use and should be stored in the frozen state. It is preferred to store the mixture in small quantities to minimize the number of times the enzyme must be thawed and refrozen.

It is preferred that the pharmacologically suitable solution be comprised of a concentrated amount of collagenase. This concentrated amount is preferred since a small but effective amount of the solution can more readily and effectively be placed in contact with the pathologic location than a larger amount of a more dilute solution. In particular, it has been found that a concentration of eight (8) units of collagenase per microliter of buffer solution is effective; however, the concentration may vary.

In the preferred embodiment the buffer solution, which is utilized is a Balanced Salt Solution produced by Alcon of Fort Worth, Tex. This saline solution contains an adequate amount of calcium ions to activate the collagenase and has an approximate pH of 8.1. It should be adjusted to a physiologically compatible pH of 7.40 before admixture with the collagenase.

It should be understood that any suitable buffer solution may be utilized. However, the solution should contain a sufficient amount of calcium ions to activate the collagenase and should not contain any compound capable of chelating the calcium ions. The collagenase manufacturer, Advance Biofactures Corp., recommends that the buffer solution have a calcium ion concentration of approximately 0.33 molar. It has been determined that a buffer solution with a lower concentration of calcium ions can be utilized and it should be understood that other solutions containing calcium ions may be used as can be determined by a reasonable amount of routine experimentation.

The following experiments conducted on rabbits are exemplary. In all experiments, "experimental solution" shall refer to the solution resulting from the admixture of collagenase (manufactured by Advance Biofactures, Corp.) with a Balanced Salt Solution (manufactured by Alcon of Fort Worth, Tex.) wherein the solution's pH is adjusted to about 7.40. The concentration of the experimental solution was eight (8) units of collagenase to one (1) microliter of Balanced Salt Solution. It should be understood that the "unit" referred to is that amount so designated by the manufacturer of Collagenase, Advance Biofactures, Corp. "Buffer Solution" shall refer to the Balanced Salt Solution with a sufficient amount of dilute hydrochloric acid added to alter the pH to 7.40.

EXPERIMENT I

Two different experiments were undertaken to demonstrate that a normal vitreous may be liquefied when contacted with a solution comprising collagen derived from Clostridiopeptidase A.

A. A Hamilton syringe was used for microliter aliquot measurements of the experimental solution. Injections were made directly into the vitreous cavity of adult New Zealand white rabbits. Prior to the injection of the enzyme containing solution, the rabbits were anesthetized with an intramuscular injection of 75 milligrams of chlorpromazine and an intramuscular injection of 50 milligrams of ketamine. After a sufficient period of time, the liquid vitreous was aspirated with a No. 22 gauge needle of a 3 cc syringe. Table 1 is a compilation of the amount of solution injected, the concentration of collagenase, the incubation time and the amount of liquid vitreous aspirated.

TABLE 1

| Microliters Injected | Units of Collagenase | Incubation Time (Min.) | Liquid Vitreous Aspirated (cc) |
|---|---|---|---|
| 10 | 40 | 30 | .5 |
| 10 | 40 | 30 | .8 |
| 10 | 40 | 60 | .8 |
| 10 | 40 | 60 | .8 |
| 20 | 80 | 15 | 1.4 |
| 20 | 80 | 30 | 1.2 |
| 20 | 80 | 30 | 1.0 |
| 10 | BSS | 30 | .5 |
| 10 | BSS | 30 | .7 |
| Insertion of plain #22 needle without injection | | | .5 |

The results illustrate that a minimum of 80 units of collagenase is required to liquefy the rabbit vitreous.

B. In the second experiment illustrating the effect of the collagenase enzyme of a normal vitreous, adult New Zealand white rabbits were sacrificed with an intravenous injection of 125 milligrams of pentabarbital. The rabbits' eyes were immediately enucleated and placed on ice. The vitreous of each eye was dissected out of the eye and placed in an individual vial. Varying quantities of the experimental solution were placed into contact with the vitreous in each vial at a temperature of 37° C. for a period of one-half hour. Immediately following the one-half hour contact period, the vials were placed in an ice bath to inactivate the collagenase. The vitreous from each vial was then poured through a plastic funnel 5 centimeters wide with a stem diameter of 0.3 cc into a monolayer of standard mesh gauze.

As each vitreous passed through the funnel, two processes were measured:

(1) Funnel passage facility; the ease of passage through the plastic funnel was visually estimated on a scale from 0 to 4+. (0 reflecting that no fluid spontaneously passed through the funnel but rather collected at the opening of the stem; 4+ indicating that all the fluid ran through the stem of the funnel quickly without any collection at the funnel stem opening.)

(2) The rate at which the vitreous filtered through the gauze was timed and measured as drops per minute and averaged over a period of five minutes. The results are tabulated in Table 2.

TABLE 2

| Units of Collagenase | Funnel Passage Facility | Gauze Filtration Rate (drops/min.) |
|---|---|---|
| Control | 0 | 1 |
| 2 | 0 | 2 |
| 4 | 0 | 2 |
| 8 | trace | 2 |
| 12 | trace-1+ | 2 |
| 20 | trace-1+ | 3 |
| 40 | 2+ | 4 |
| 80 | 4+ | 6 |

The results indicate that a significant amount of liquifaction occurred when the vitreous was contacted with 80 units of collagenase.

EXPERIMENT II

In order to test the effect of collagenase on intraocular scar formation, another experiment was performed. In this experiment, three adult New Zealand white rabbits were anesthetized with a 75 milligram intramuscular injection of chlorpromazine and an intramuscular injection of 50 milligrams of ketamine. Blood was taken from the leg vein of each rabbit and 0.2 ccs. of this autologous blood was injected into the vitreous of each eye.

The resulting hemorrhages were left untouched for 18 weeks in order to allow intravitreal scars to form. After this initial period, 240 units of collagenase (30 microliters of the experimental solution) were injected into half of the eyes and the other half were injected with a buffer solution. One-half hour after the injection, the animals were sacrificed and the eyes were immediately enucleated and placed in a fixative solution. Photographs were taken and light and electron microscopy were performed. This data indicated that the vitreous scars had been lysed.

EXPERIMENT III

An experiment was undertaken to illustrate the effect of collagenase injected into the anterior chamber. Two adult New Zealand white rabbits were anesthetized in the same manner as described in EXPERIMENT II. 0.1 cc of aqueous fluid was aspirated from the anterior chambers of both rabbits, using a No. 27 gauge needle and a 1 cc syringe. Then, using a microliter syringe, varying amounts of the experimental solution were injected into the anterior chamber using the same peripheral corneal incision created by the No. 27 gauge needle. One animal (Rabbit 1) was observed after 24 hours, 48 hours, one week, and then one month. The other animal (Rabbit 2) was observed after 24 hours, 48 hours; then, Rabbit 2 was sacrificed.

The results were as follows:

Rabbit No. 1:

Right Eye: 50 units of collagenase (6.25 microliters of experimental solution) were injected. There was no corneal or lens clouding at any time. There was no visible inflammation in the anterior chamber and the iris appeared normal. There was no change in the normal appearance of the anterior segment for one month.

Left Eye: 100 units of collagenase (12.5 microliters of experimental solution) were injected. On visual inspection, there were no corneal changes. There was one small hemorrhage on the inferior iris with mild inflammation in the anterior chamber. At 48 hours, a posterior senechia had formed nasally between the iris and the lens. At one month, the cornea and lens appeared clear.

Rabbit No. 2:

Right Eye: 80 units of collagenase (10 microliters of experimental solution) were injected. Visual observation indicated that there were no corneal or lens changes. Some mild inflammation of the anterior chamber was observed.

Left Eye: 160 units of collagenase (20 microliters of experimental solution) were injected. Visual observation did not reveal any corneal or lens changes. A moderate inflammatory reaction in the anterior chamber was observed.

These results indicate that 160 units of collagenase can be tolerated by the anterior segment structures without any significant deleterious effects to normal visual function.

EXPERIMENT IV

An experiment was run to illustrate the effect of an intravitreal injection of collagenase on the retinal structure. In this experiment, three adult New Zealand white rabbits were anesthetized as previously described in EXPERIMENT II and 240 units of collagenase (30 microliters of experimental solution) were injected into the vitreous cavity of three of the eyes. The remaining eyes were injected with 30 microliters of a buffer solution. One-half hour after the injection, the animals were sacrificed and the eyes were immediately enucleated and placed in a fixitive. Electron microscopy did not show any difference in the retinal structure between the control eyes and the treated eyes. However, there was a definite destruction of the fibrillar structure of the vitreous both in the overlying retinal blood vessels and in the retinal periphery.

EXPERIMENT V

This experiment was run to demonstrate the effect of intravitreal injections of collagenase on retinal function. One adult New Zealand white rabbit was anesthetized as described in EXPERIMENT II. Four hundred units of collagenase (50 microliters of the experimental solution) were injected into the vitreous cavity of the right eye. One-half hour later, a double-barrel irrigation/aspiration needle was inserted into the vitreous cavity. The irrigation aperture was a No. 22 gauge needle size and the aspiration aperture was a No. 18 gauge needle size. The irrigation cannula of the needle was connected to a bag of normal saline solution; the aspiration cannula was connected to a peristaltic pump. A total of 15 ccs. of normal saline was infused and aspirated through the vitreous. An operating microscope with a fundus contact lens was used for the procedure.

After the termination of the procedure in the right eye, the vitreous cavity of the left eye was irrigated/aspirated with normal solution alone. One week later, electroretinography was performed in both eyes. The electroretinogram for each eye was fully normal.

It should be understood that other tests have led to the following conclusions:

The injection of any substance, for example a buffer solution, into the vitreous appears to affect retinal function within a short time after injection as determined by electroretinography. However, visual observation and microscopy do not reveal any retinal damage. Indeed, retinal function appears normal, as determined by electroretinography one week after injection. Accordingly, it is believed that no permanent retinal damage results; rather, it is believed that the substance injected causes transient supression of retinal activity which appears to last for approximately one week.

EXPERIMENT VI

This experiment was included to illustrate the effects of long-term incubation of the intravitreal injection of collagenase on retinal structure and function. In this experiment, one adult New Zealand white rabbit was anesthetized as described in Experiment II. One eye was injected with 400 units of collagenase (50 microliters of the experimental solution). The other eye was injected with 50 microliters of the buffer solution alone. Electroretinography performed both 24 hours and one week after the injection of the collagenase showed a marked suppression of retinal electrical activity. Visual examination of the eye injected with the collagenase containing solution after the sacrifice of the animal showed severe hemorrhaging in the vitreous and detachment of the retina.

EXPERIMENT VII

This experiment was included to illustrate the effect of a collagenase inhibitor on retinal function. One milligram of acetylcysteine was injected into the vitreous cavity of an adult New Zealand rabbit which had been anesthetized as described in EXPERIMENT II above. A buffer solution alone was injected into the other eye. Electroretinography was performed one day, one week and one month postoperatively and showed complete supression of retinal electrical activity in the eye treated with acetylcysteine.

In summary, the above experiments on rabbits are illustrative of the following:

(1) At least 80 units of collagenase are required to significantly liquefy the vitreous.

(2) Vitreous scars are lysed by contacting the scars for one-half of an hour with 240 units of collagenase.

(3) 160 units of collagenase can be tolerated by the anterior segment structures without significantly affecting normal visual function.

(4) 240 units of collagenase dissolves hemorrhages and causes no damage to the retina as demonstrated in electron microscopy.

(5) 400 units of collagenase injected into the vitreous and removed after one-half of an hour causes no functional retinal damage as determined by electroretinography.

(6) When 400 units of the collagenase enzyme is injected into the vitreous and not removed, it causes hemorrhaging and retinal damage.

(7) Collagenase inhibitors containing metal chelators do destroy retinal function.

While the above experiments were conducted on rabbits, the results are indicative of what can be anticipated with all mammals. This invention may be practiced on any animal including a human.

A rabbit's ocular region is similar to a human's in that they both contain many collagen rich structures. The rabbit cornea, anterior chamber and lens structure is similar to the corresponding human structures. The rabbit vitreous is more viscous than the vitreous of a human, but the human vitreous is approximately five (5) times the size of the rabbit vitreous. The rabbit retina is different from the human retina in that the rabbit's retinal blood vessels extend into the vitreous while the human's vessels are disposed within the retina.

In a human, the concentration of the pharmacologically suitable solution may be the same as the concentration utilized with other mammals. What is important is to contact those collagen fibrils sought to be lysed. With higher concentrations, small amounts may be injected by use of a microliter syringe. If a dilute solution were used, the injection of an effective amount of collagenase would require the injection of a larger quantity of solution which would not be as effective as a concentrated amount.

Accordingly, it is preferred to utilize a small but effective amont of a pharmacologically suitable solution comprising a concentrated amount of collagenase. Too high a concentration may damage ocular structures not intended to be affected, while too low a concentration may not be effective. The concentration of collagenase in the solution can be varied but may be determined with a reasonable amount of routine experimentation. The following factors should be considered in determining the concentration of collagenase in the pharmacologically suitable solution: the mammal to be injected; the amount, location and nature of the collagen fibrils to be lysed; and the nature and proximity of other collagen rich structures adjacent the collagen fibrils to be lysed.

As previously stated, the amount and concentration of the pharmacologically suitable solution utilized will vary depending on many factors. For example, prior to pars plana vitrectomy on a human the collagen fibrils of the vitreous could be lysed in accordance with this invention; however, the amount of solution required to liquefy or lyse the fibrils would be more than that required to lyse a rabbit vitreous since, in the latter instance, the vitreous is approximately five times smaller in volume than a human vitreous.

In view of the preceding description, further modifications and alternative embodiments of the instant invention will be apparent to those skilled in the art. Accordingly, the preceding description is to be construed as explanatory and illustrative only and is for the purpose of teaching and enabling those skilled in the art to practice this invention. It should be understood that the amount of the pharmacologically suitable solution required for the lysis of collagen fibrils will vary and the period of time necessary for the collagenase solution to contact the collagen fibrils will vary. Suitable amounts and times can be determined from a reasonable amount of experimentation and the following factors should be considered: the mammal injected; the concentration of collagenase in the solution; the type of collagenase used; the amount, location and nature of the collagen fibrils to be lysed; and the nature and proximity of other collagen rich structures adjacent the collagen fibrils to be lysed.

While the preferred embodiment of the above described invention is to be understood to be the best mode presently contemplated, it is by no means the only embodiment possible. The scope of the invention is defined by the following claims and by any equivalent modifications and variations that fall within the true spirit of the invention.

What is claimed is:

1. A method for the selective lysis of collagen fibrils located in the vitreous of the ocular region of a mammal comprising:
   injecting intravitreally a small but effective amount of a pharmacologically suitable solution comprising a concentrated amount of collagenase;
   contacting said fibrils with said solution;
   flushing the intravitreal region by injecting an effective amount of an inactivator of collagenase solution; and
   removing said collagenase solution from said intravitreal region before said solution damages other ocular structures not intended to be affected thereby.

2. The method of claim 1 wherein said steps of injecting an inactivator of collagenase solution and removing said collagenase solution are performed substantially simultaneously.

3. A method for the selective lysis of collagen fibrils located in the vitreous of the ocular region of a mammal comprising:
   preparing a pharmacologically suitable solution comprising collagenase produced from the bacterium *Clostridium histolyticum* by addmixing a concentrated amount of said collagenase with a solution having a pH of about 7.40 and containing a sufficient amount of calcium ions to activate said collagenase;
   injecting intravitreally a small but effective amount of said pharmacologically suitable solution comprising a concentrated amount of collagenase;
   flushing the intravitreal region by injecting an effective amount of an inactivator of collagenase solution; and
   removing said collagenase from said intravitreal region before said solution damages other ocular structures not intended to be affected thereby.

4. The method of claim 3 wherein said steps of injecting an inactivator of collagenase solution and removing said collagenase solution are performed substantially simultaneously.

5. A method for the selective lysis of collagen fibrils located in the anterior chamber of the ocular region of a mammal comprising:
   injecting into said anterior chamber a small but effective amount of a pharmacologically suitable solution comprising a concentrated amount of collagenase;
   contacting said fibrils with said solution; and
   removing said collagenase solution from said anterior chamber before said solution damages other ocular structures not intended to be affected thereby.

6. The method of claim 5 wherein said collagenase is naturally removed from said anterior chamber.

* * * * *